US010625016B2

(12) United States Patent
Amon et al.

(10) Patent No.: US 10,625,016 B2
(45) Date of Patent: Apr. 21, 2020

(54) INFUSION DEVICE

(71) Applicant: Fresenius Vial SAS, Brézins (FR)

(72) Inventors: Barbara Amon, Idstein (DE); Michael Becker, Knittlingen (DE)

(73) Assignee: Fresenius Vial SAS, Brézins (FR)

( * ) Notice: Subject to any disclaimer, the term of this patent is extended or adjusted under 35 U.S.C. 154(b) by 0 days.

(21) Appl. No.: 15/549,287

(22) PCT Filed: Mar. 2, 2016

(86) PCT No.: PCT/EP2016/054346
§ 371 (c)(1),
(2) Date: Aug. 7, 2017

(87) PCT Pub. No.: WO2016/146381
PCT Pub. Date: Sep. 22, 2016

(65) Prior Publication Data
US 2018/0028745 A1 Feb. 1, 2018

(30) Foreign Application Priority Data
Mar. 13, 2015 (EP) .................................... 15290067

(51) Int. Cl.
*A61M 5/142* (2006.01)
*A61M 5/14* (2006.01)

(52) U.S. Cl.
CPC ...... *A61M 5/14244* (2013.01); *A61M 5/1413* (2013.01); *A61M 5/1415* (2013.01);
(Continued)

(58) Field of Classification Search
CPC .......... A61M 5/141244; A61M 5/1413; A61M 5/1415; A61M 5/14232; A61M 5/14248;
(Continued)

(56) References Cited

U.S. PATENT DOCUMENTS 4,398,908 A * 8/1983 Siposs ................... A61M 5/142
128/DIG. 12
4,559,038 A * 12/1985 Berg ..................... A61M 5/142
417/474
(Continued)

FOREIGN PATENT DOCUMENTS

| CN | 204089910 U | 1/2015 |
|----|-------------|--------|
| EP | 1563859 A1 | 8/2005 |

(Continued)

OTHER PUBLICATIONS

International Search Report and Written Opinion, counterpart PCT Appl. No. PCT/EP2016/054346, 20 pages (dated Jul. 15, 2016).
(Continued)

*Primary Examiner* — Nathan R Price
*Assistant Examiner* — Mark A Igel
(74) *Attorney, Agent, or Firm* — Cook Alex Ltd.

(57) ABSTRACT

An infusion device (1)comprises a housing (10)having a front side (102)and a back side (103)opposite to the front side (102). A display device (11)is arranged at the front side (102)of the housing (10). A pump mechanism (18)serves to act onto a disposable pump module (17, 4), the pump mechanism (18)being included in the housing (10). Herein, the housing (10)is constituted to receive the disposable pump module (17, 4)at the back side (103). In this way an infusion device is provided which allows placing a disposable pump module on the housing of the infusion device and which may offer space savings over existing infusion devices.

9 Claims, 7 Drawing Sheets

(52) U.S. Cl.
CPC .... *A61M 5/14232* (2013.01); *A61M 5/14248* (2013.01); *A61M 2005/14268* (2013.01); *A61M 2205/12* (2013.01); *A61M 2205/121* (2013.01); *A61M 2205/123* (2013.01); *A61M 2205/3561* (2013.01); *A61M 2205/502* (2013.01); *A61M 2205/505* (2013.01); *A61M 2205/8206* (2013.01); *A61M 2205/8237* (2013.01); *A61M 2209/082* (2013.01); *A61M 2209/084* (2013.01); *A61M 2209/086* (2013.01)

(58) Field of Classification Search
CPC .... A61M 2205/14268; A61M 2205/12; A61M 2205/121; A61M 2205/123; A61M 2205/3561; A61M 2205/502; A61M 2205/505; A61M 2205/8206; A61M 2205/8237
See application file for complete search history.

(56) References Cited

U.S. PATENT DOCUMENTS

| | | | | |
|---|---|---|---|---|
| 4,863,425 A | * | 9/1989 | Slate | A61M 5/16854 604/65 |
| 5,083,908 A | * | 1/1992 | Gagnebin | A61M 5/14232 417/477.1 |
| 5,478,211 A | * | 12/1995 | Dominiak | A61M 5/142 417/234 |
| 5,630,710 A | * | 5/1997 | Tune | A61M 5/172 417/326 |
| 5,658,133 A | * | 8/1997 | Anderson | A61M 5/172 417/63 |
| 5,984,894 A | | 11/1999 | Poulsen et al. | |
| 6,165,154 A | | 12/2000 | Gray et al. | |
| 2004/0127840 A1 | * | 7/2004 | Gara | A61M 1/3683 604/4.01 |
| 2006/0140798 A1 | * | 6/2006 | Kutsuzawa | A61M 5/16831 417/474 |
| 2008/0009824 A1 | | 1/2008 | Moberg et al. | |
| 2008/0267599 A1 | * | 10/2008 | Arnold | A61F 7/0085 392/470 |
| 2010/0082011 A1 | * | 4/2010 | Lewis | A61M 5/14232 604/503 |
| 2011/0133946 A1 | * | 6/2011 | Kopp | A61M 5/142 340/679 |
| 2012/0163999 A1 | * | 6/2012 | Becker | A61M 5/1413 417/53 |
| 2012/0207635 A1 | | 8/2012 | Becker | |
| 2013/0144254 A1 | | 6/2013 | Amirouche et al. | |
| 2013/0274576 A1 | | 10/2013 | Amirouche et al. | |
| 2014/0188076 A1 | | 7/2014 | Kamen et al. | |
| 2014/0276553 A1 | * | 9/2014 | Rosinko | A61M 5/14244 604/504 |
| 2016/0158519 A1 | * | 6/2016 | Rhinehart | A61M 5/007 604/535 |

FOREIGN PATENT DOCUMENTS

| | | | |
|---|---|---|---|
| EP | 2962714 A1 | 1/2016 | |
| WO | WO-8500523 A1 * | 2/1985 | ........ A61M 5/14244 |
| WO | WO 2008/024808 A2 | 2/2008 | |
| WO | WO 2012/049263 A1 | 4/2012 | |
| WO | WO 2014/201358 A2 | 12/2014 | |

OTHER PUBLICATIONS

Office Action issued by the Chinese Patent Office for Chinese Application No. 201680014433 dated Dec. 4, 2019, with English translation (12 pages).
Search Report of the Chinese Patent Office for Chinese Application No. 201680014433 dated Nov. 25, 2019 (2 pages).

* cited by examiner

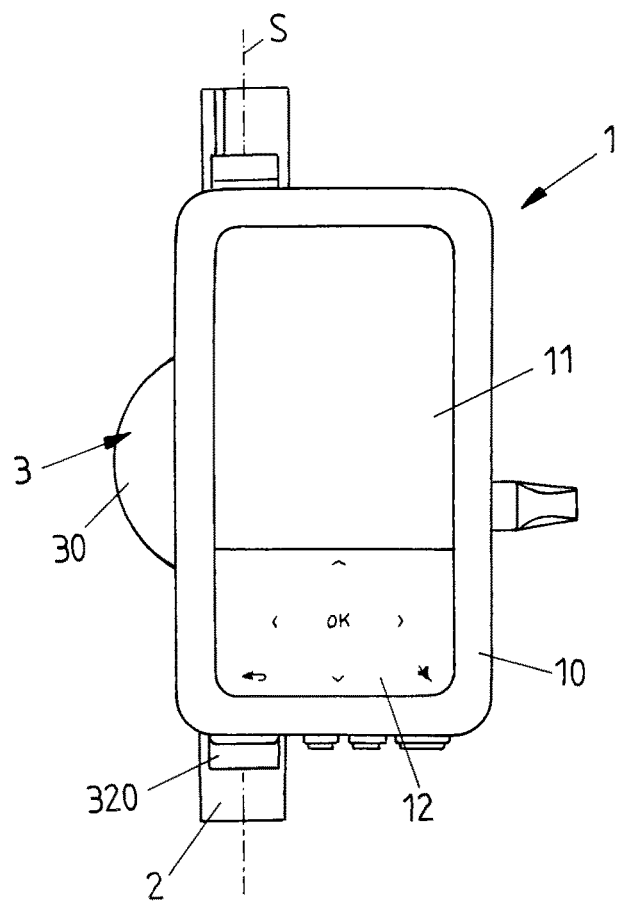
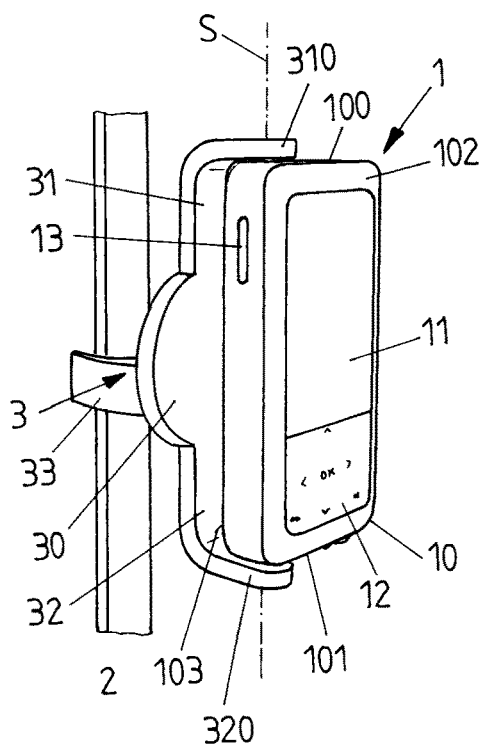
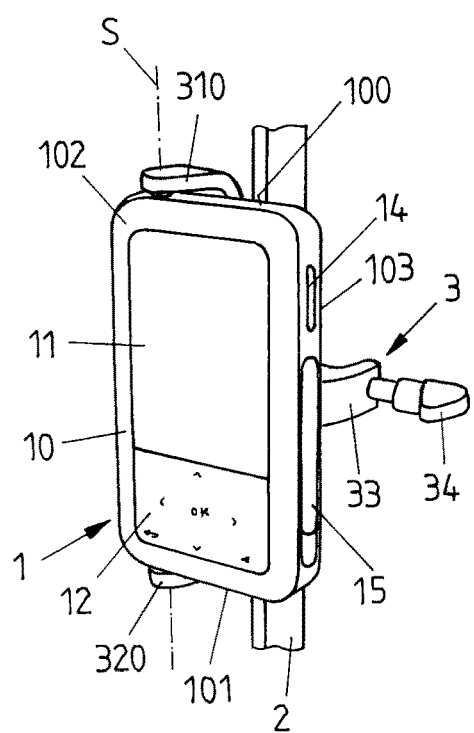

INFUSION DEVICE

The present application is a U.S. National Stage of PCT International Patent Application No. PCT/EP2016/054346, filed Mar. 2, 2016, which claims priority to EP Application No. 15290067.6, filed Mar. 13, 2015, both of which are hereby incorporated herein by reference.

The invention relates to an infusion device according to the preamble of claim 1. An infusion device generally serves to administer a medical fluids, for example drugs, standard infusion solution, clinical nutritional liquids or the like, to a patient.

An infusion device of this kind comprises a housing having a front side and a back side opposite to the front side. A display device is arranged at the front side of the housing. A pump mechanism for acting onto a disposable pump module is included in the housing.

An infusion device having a pump mechanism is for example known from WO 2012/049263 A1. The pump mechanism in this infusion device comprises a wobble device constituted to perform a wobbling pump action for acting onto a membrane of a disposable pump module. By locally depressing the membrane in a revolving fashion, a liquid is pumped through a pump channel of the disposal pump module for delivering a medical fluid to a patient.

There is a desire for infusion devices being small in size such that they can be arranged in an organized, space-efficient manner for example at a bedside of a patient in a hospital. In particular in an intensive care unit of a hospital possibly a large number of infusion devices are used on a patient and therefore must be placed at the bedside of the patient such that infusion devices small in size may offer advantages over existing infusion devices.

From US 2011/133946 A an infusion pump device is known including a replaceable cassette connected to a control module. The cassette may include a reservoir containing a medication that is to be delivered to a patient. Tubing can extend from the cassette and may be in communication with an infusion set or catheter to deliver the medication to the patient.

From US 2006/140798 A an infusion device is known having a door which may be pivoted with respect to a housing. A display is placed on the door and can be pivoted together with the door. By opening the door, an infusion set may be placed on the housing.

From US 2010/082011 A an infusion device is known having a door hinged to a housing and being pivotable between a closed position and an opened position. In the opened position, a disposable feeding set may be arranged on a side of the housing.

It is an object of the instant invention to provide an infusion device which allows placing a disposable pump module on the housing of the infusion device and which may offer space savings over existing infusion devices.

This object is achieved by means of an infusion device comprising the features of claim 1.

Accordingly, the housing of the infusion device is constituted to receive the disposable pump module at its back side.

In this way, the infusion device may be built in a space-efficient manner having a flat shape, i.e., having a small thickness (corresponding—at least approximately to the distance between the front side and the back side) as compared to its height (measured in a vertical direction in a normal use position of the infusion device). By placing the disposable pump module at the back side of the housing, it is not necessary to access the front side of the housing for placing the disposable pump module on the infusion device.

The housing comprises, at its front side, a display device and further encloses a pump mechanism. The pump mechanism acts onto the disposable pump module for pumping a medical fluid through the pump module or out of the pump module. The disposable pump module can be attached to the housing at its back side and, in an operative state of the infusion device, is fixedly held on the housing such that a medical fluid can be pumped through the disposable pump module or out of the disposable pump module.

In one embodiment, a back part is connectable to the housing. The back part may be pivotable with respect to the housing when it is connected to the housing. To exchange the back part by another back part, the back part may be released from the housing such that it can be taken off the housing to connect another back part to the housing.

The back part, when it is connected to the housing, beneficially can be pivoted with respect to the housing between an opened position and a closed position. In the closed position, the back part is approached to the housing and covers at least a portion of the back side of the housing. In the closed position, hence, the infusion device assumes a compact shape.

The disposable pump module may be attached to the housing in different ways.

In a first variant, the back part together with the housing may be constituted to receive the disposable pump module in-between them such that the disposable pump module is held in-between the housing and the back part in the closed position of the back part. For this, the back part and/or the back side of the housing may comprise a reception opening for receiving the disposable pump module. For attaching the disposable pump module to the infusion device, for example a pump cassette of the disposable module may be inserted into the reception opening when the back part is in its opened position. By closing the back part the disposable pump module is connected to the infusion device such that in an operative state of the infusion device the disposable pump module is fixedly held on the infusion device.

In another, second variant, the disposable pump module may be constituted by the back part itself. The disposable pump module, in the shape of the back part, hence may be attached to the housing of the infusion device by connecting it directly to the housing. The back part, in this case, may for example comprise a fluid container containing a medical fluid which shall be administered to a patient. The back part, hence, as a whole is disposable and can be attached to the housing. Once the fluid container has been emptied in that the medical fluid which has been contained in it has been delivered to the patient, the back part is disconnected from the housing, can be disposed and can be replaced by another back part.

The back part, in this case, may comprise a connector for attaching an infusion line through which the medical fluid may be delivered to the patient.

The pump mechanism is included in the housing and acts onto the disposal pump module for pumping a medical fluid through the disposable pump module or out of the disposable pump module. The pump mechanism may, for example, comprise a wobble device for performing a wobbling movement for acting onto the disposable pump module, as it is described in WO 2012/049263 A1 which shall be incorporated herein by reference. A wobbling pump mechanism of this kind may allow for a construction of the infusion device having a small size and a flat shape. In particular, the infusion device may have a flat shape resembling the shape and size of a smart phone or PDA as commonly known today. This for example allows infusion devices to be easily carried around in a pocket or the like such that infusion devices may easily be moved from one place to another.

The infusion device may furthermore comprise a battery device for storing electrical energy. The battery device may be constituted to allow operation of the infusion device without the infusion device being connected to an external power supply line. Hence, actual operation of the infusion device, i.e., an actual infusion operation, may be carried out in an autarkic manner without connection to an external power supply.

The battery device, beneficially, is rechargeable. The infusion device for this may be connected to a charging station, for example in the shape of a docking station on which the infusion device can be placed. Once the battery device is charged, a user may remove the infusion device from the docking station and may use it to perform an actual infusion operation on a patient.

A system comprises an infusion device of the kind described above and a holding device for holding the infusion device for example on a stand. The holding device, in one embodiment, is constituted to hold the infusion device such that the infusion device can be pivoted with respect to the holding device about a first pivot axis.

The holding device serves to fixedly arrange the infusion device for example at the bedside of a patient. By means of the holding device, the infusion device may for example be connected to a stand or to a bed post of a patient's bed. By pivoting the infusion device as a whole with respect to the holding device, the infusion device may be brought into a comfortable use position for a user which for example allows easy access to the display device arranged on the front side of the housing. In addition, by pivoting the infusion device with respect to the holding device, a user may gain access to the back side of the housing to place a disposable pump module on the housing to bring the infusion device into an operative state ready for performing an infusion operation.

In one embodiment, the holding device comprises a base and at least one arm extending from the base in a direction parallel to the first pivot axis about which the infusion device is pivotable with respect to the holding device. The at least one arm carries a connection finger at an end opposite to the base. To the connection finger the infusion device can be connected such that the infusion device is pivotable with respect to holding device.

In one embodiment, the holding device comprises two arms which extend from the base in opposite directions. Each arm carries a connection finger at an end opposite to the base, the connection fingers of the arms being constituted to receive the infusion device in-between them such that the infusion device can be pivoted about the first pivot axis with respect to the connection fingers.

In one embodiment, the connection finger of the first arm may be constituted to reach around a top side of the infusion device, whereas the connection finger of the other, second arm is constituted to reach around an opposite, bottom side of the infusion device. The connection fingers, hence, engage with opposite sides of the infusion device, for example by engaging into mounting recesses at the top side and the bottom side of the infusion device, respectively. For arranging the infusion device on the holding device, the infusion device may be inserted in-between the connection fingers of the arms of the holding device until the connection fingers snappingly engage the infusion device in a positive locking manner. For removing the infusion device from the holding device, one of the connection fingers may be slightly bent such that the positive locking engagement is released and the infusion device can be detached from the holding device.

The holding device, in one embodiment, comprises a clamping device for connecting the holding device for example to a stand or to a bed post of a patient's bed. The clamping device may, for example, comprise a clamping screw by means of which a clamping connection of the holding device and the stand or the bed post can be established.

In one embodiment, the base of the holding device may be pivotably connected to the clamping device such that the base of the holding device can be pivoted with respect with respect to the clamping device. Herein, the base is pivotable about a second pivot axis which is directed transversely to the first pivot axis. Hence, by pivoting the infusion device about the first pivot axis with respect to the holding device and/or by pivoting the base of the holding device with respect to the clamping device, the position of the infusion device may be adapted as a user deems it fit.

The idea underlying the invention shall subsequently be described in more detail with respect to the embodiments shown in the figures. Herein:

FIG. 1 shows a front view of an infusion device placed on a holding device;

FIG. 2A shows a perspective view of the infusion device on the holding device;

FIG. 2B shows another perspective view of the infusion device on the holding device;

FIG. 1 and FIG. 2A, 2B show an embodiment of an infusion device 1 constituted to administer a medical fluid, for example a drug, a nutritional feeding solution or another solution, to a patient. The infusion device 1 is arranged on a holding device 3 and, via the holding device 3, on a stand 2.

Figure 3:
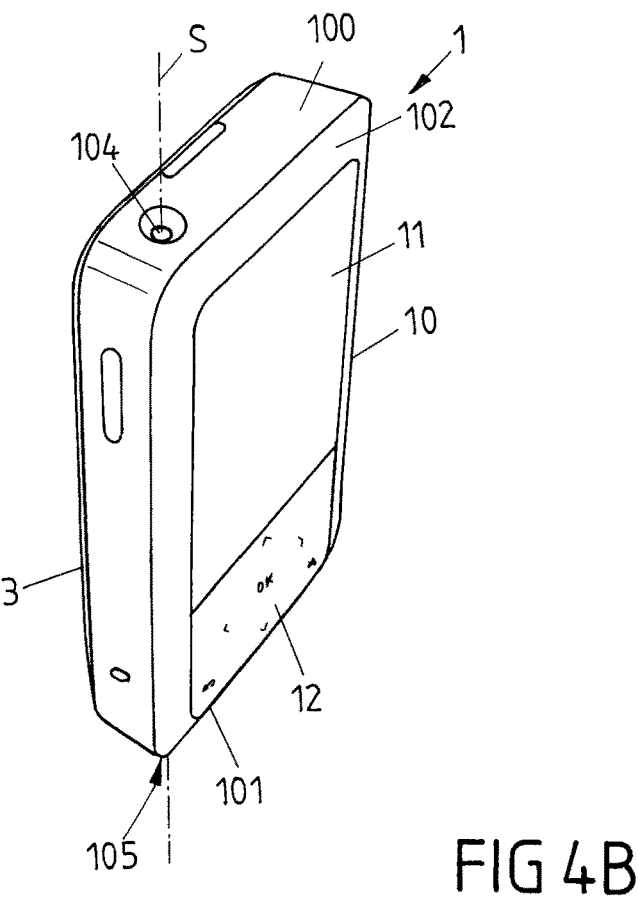
FIG. 3 shows a separate view of the infusion device.
Figure 4A:
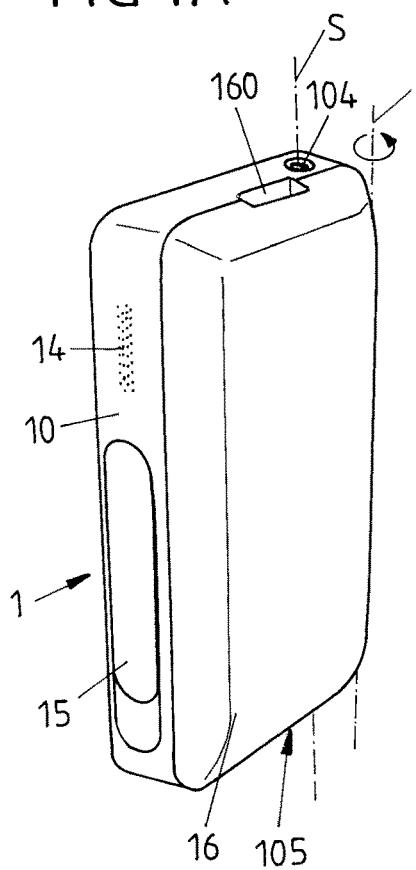
FIG. 4A shows a back view of the infusion device, with a first type of back part arranged on a back side of a housing of the infusion device.
Figure 4B:
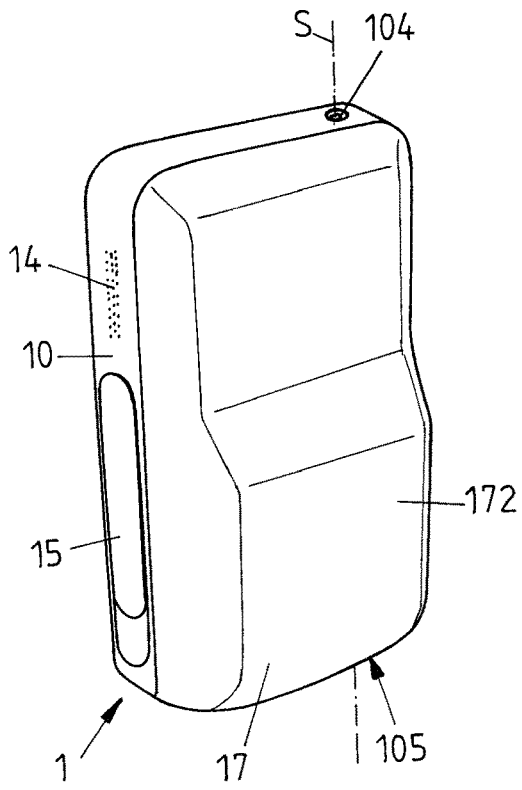
FIG. 4B shows a back view of the infusion device with a second type of back part arranged on the housing.

The infusion device 1, as it is shown in FIGS. 1 and 2A, 2B and in separate views in FIGS. 3 and 4A, 4B has a flat shape resembling the shape of a smart phone or a personal digital assistant (PDA) as they are commonly known today. In particular, the infusion device 1 has a rather small thickness (measured between a front side 102 and a back side 103 of a housing 10) as compared to its height (measured along the vertical direction) and width (measured along a transverse direction).

The housing 10 encloses a pump mechanism for performing a peristaltic pump action and carries, at its front side 102, a display device 11, for example in the shape of a touch-sensitive display. Further, at the front side 102 an input device 12 having a multiplicity of keys is arranged. Via the input device 12 and the display device 11 located on the front side 102 of the housing 10, a user may input control commands into the infusion device 1 and may receive operational information, for example about an ongoing infusion operation.

Furthermore, at transverse sides of the housing 10 keys or bottoms 13, 15 and a loudspeaker 14 may be arranged.

The infusion device 1 is fixedly held on a holding device 3 and via the holding device 3 on the stand 2. The holding device 3 comprises a base 30 from which arms 31, 32 extend in opposite directions. Each arm 31, 32, at opposite ends, carries a connection finger 310, 320 reaching around the infusion device 1 at a top side 100 and a bottom side 101 of the housing 10. The connection fingers 310, 320 engage with mounting recesses 104, 105 at the top side 100 respectively the bottom side 101 such that the infusion device 1 is held in-between the connection fingers 310, 320 in a positive locking manner.

Herein, by engaging the mounting recesses 104, 105, a pivotable mounting is provided allowing the infusion device 1 to be pivoted about a pivoting axis S with respect to the holding device 3. In this way, the infusion device 1 may be pivoted by a user to bring it in a position which, for example, allows a comfortable, convenient access to the input device 12 and a comfortable view on the display device 11.

The base 30 of the holding device 3 is connected to a clamping device 33 via which the holding device 3 is connected to the stand 2 in a clamping fashion. The clamping device 33 comprises a clamping screw 34 by which a clamping connection between the clamping device 33 and the stand 2 can be established.

Figure 6:
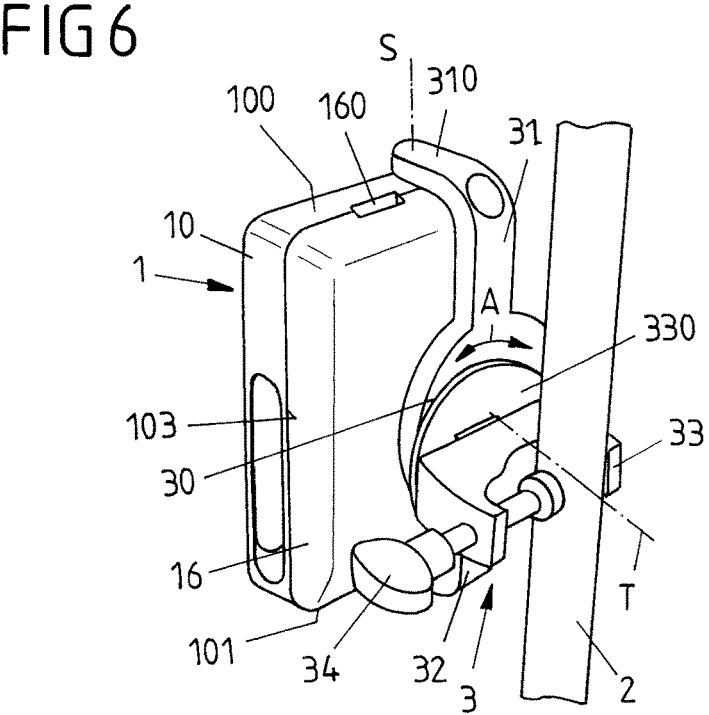
FIG. 6 shows a back view of the infusion device on the holding device.

Beneficially, as indicated in FIG. 6, the base 30 may be pivotable with respect to a connection piece 330 of the clamping device 33 about a pivoting axis T along a pivoting direction A such that the position of the base 30 and with it the position of the arms 31, 32 may be adjusted with respect to the clamping device 33. The infusion device 1, hence, is pivotable with respect to the holding device 3 about the pivoting axis S. In addition, the base 30 can be pivoted with respect to the clamping device 33 about the pivoting axis T directed transversely to the pivoting axis S such that the pivoting position of the infusion device 1 may be adjusted about two separate axes.

The infusion device 1 may be equipped with different back parts 16, 17, as it is shown in FIGS. 4A and 4B. In this way, the infusion device 1 may be adapted to receive different disposable pump modules.

Figure 5:
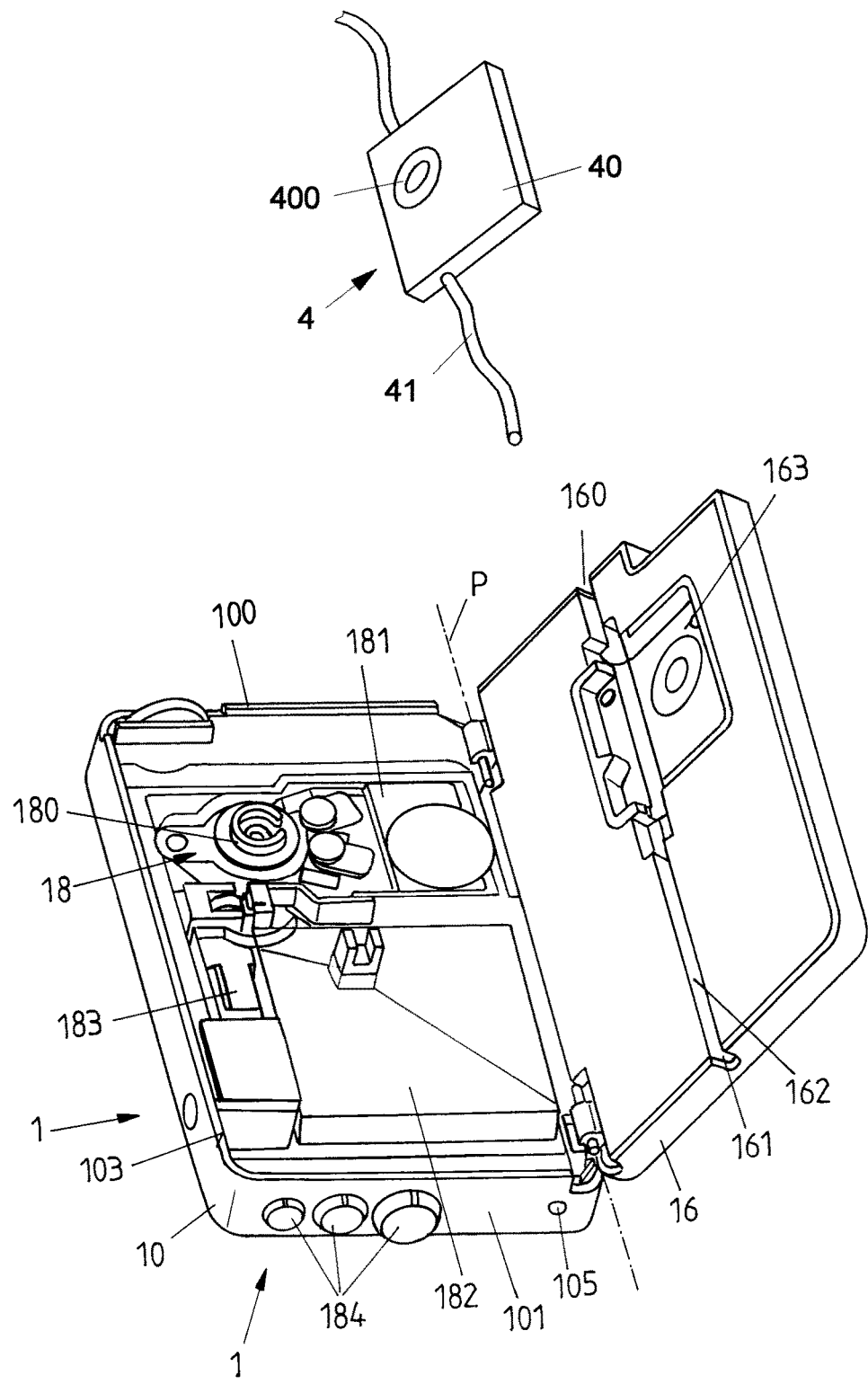
FIG. 5 shows a partially cut-free view of the infusion device, with a back part of the first type in an opened position.

For example, the back part 16 of FIG. 4A is adapted to place a disposable pump module 4 in the shape of an infusion set, as it is shown for example in FIG. 5, on the back side 103 of the housing 10. The back part 16 can be pivoted about a pivoting axis P with respect to the housing 10 and may be moved between an opened position (FIG. 5) and a closed position (FIG. 4A).

In the opened position the disposable pump module 4 may be placed with a pump cassette 40 in a reception opening 163 at the inside of the back part 16 such that an infusion line 41 extending from the pump cassette 40 is received in a reception channel 162 of the back part 16, the infusion line 41 entering the reception channel 162 at an opening 160 and exiting the reception channel 162 at an opening 161. To secure the disposal pump module 4 on the infusion device 1, the back part 16 may then be pivoted about the pivoting axis P into its closed position in which the disposable pump module 4 is received in-between the back part 16 and the housing 10 and, in this way, is securely fastened on the infusion device 1.

In this first variant, the back part 16 serves to secure a disposable pump module 4 in the shape of an infusion set on the infusion device 1. The back part 16 may be released from the housing 10 and may be replaced by another back part 17, as it is for example shown in FIG. 4B.

The back part 17 of FIG. 4B itself constitutes a disposable pump module. The back part 17 comprises a fluid container 172 and, hence, contains a medical fluid. To the back part 17 an infusion line may be attached for delivering the medical fluid contained in the fluid container 172 towards a patient.

Once the fluid container 172 is emptied, the back part 17 can be removed from the housing 10 and can be disposed. Another infusion operation may then be performed by using another back part 16, 17.

FIG. 5 shows the housing 10 without a cover at its back side 103 to make the components enclosed in the housing 10 visible. As it is shown in FIG. 5, the housing 10 encloses a pump mechanism 18 comprising a wobble device 180 which is driven by a drive device 181 in the shape of an electric motor. The wobble device 180 may be constituted for example as described in WO 2012/049263 A1 and is constituted to perform a wobbling, revolving movement to locally depress a membrane 400 of a disposable pump module 4 in a revolving fashion. Besides the drive device 181 a battery device 182 in the shape of a rechargeable battery is enclosed in the housing 10 for supplying electrical energy to the drive device 181 during operation of the infusion device 1. An actuation mechanism 183 serves to actuate a valve mechanism of the pump cassette 40 to open a fluid path through the pump cassette 40.

At the bottom side 101 of the housing 10 connectors 184 are placed which allow connecting for example an electrical supply line or communication lines to the infusion device 1.

FIG. 5 shows the infusion device 1 with a back part 16 connected to the housing 10 for receiving a disposable pump module 4 in the shape of an infusion set. In the closed position of the back part 16 the pump cassette 40 of the disposable pump module 4 is received in the reception opening 163 at the inside of the back part 16 such that the wobble device 180 abuts the membrane 400 for acting onto the membrane 400 in order to pump a medical fluid through the disposable pump module 4. The disposable pump module 4 may, for example, be connected to a fluid container such as a medication bag such that a medical fluid may be pumped through the infusion line 41 via the infusion device 1 towards a patient.

Figure 9C:
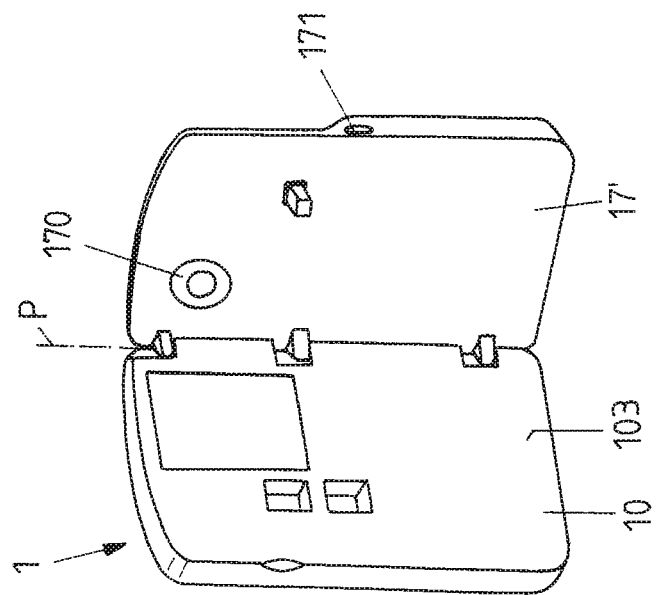
FIG. 9C shows a back view of the infusion device, with the back part being opened.
Figure 9B:
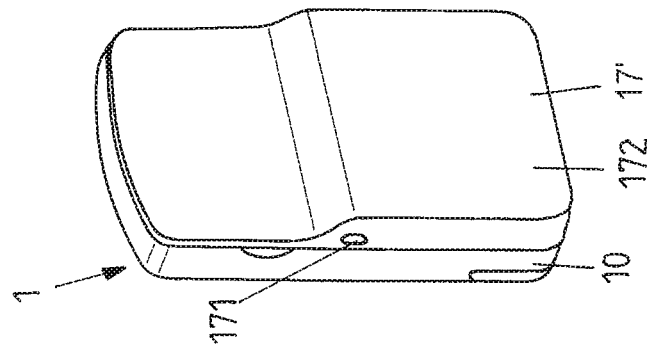
FIG. 9B shows a back view of the infusion device.
Figure 9A:
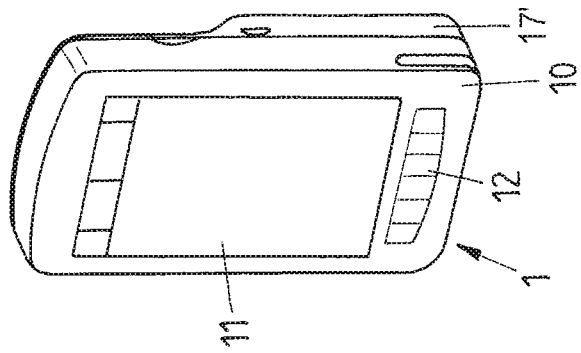
FIG. 9A shows the infusion device of FIG. 8A-8C, with another type of back part.

If a back part 17 of the second type is used on the housing 10, the back part 17 comprises a membrane 170 (see FIG. 9C) which in a closed, connected state of the back part 17 is in a position to interact with the wobble device 180 to pump a medical fluid out of the back part 17.

Figure 7:
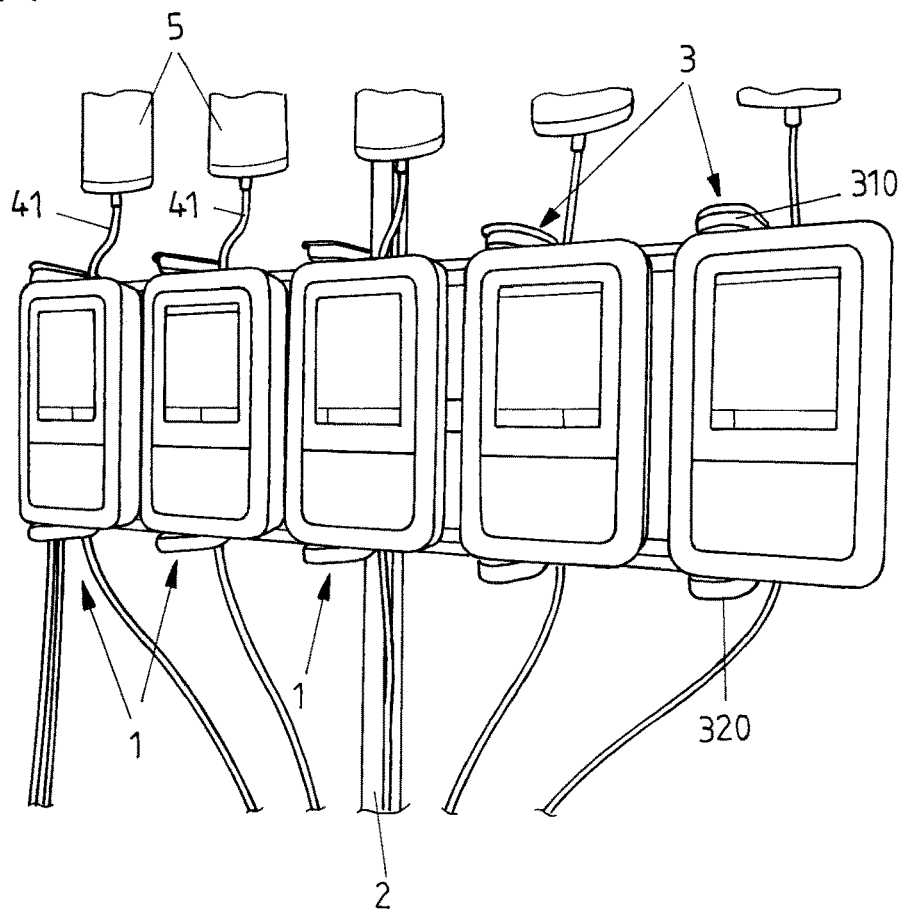
FIG. 7 shows a view of multiple infusion devices arranged on a stand.

Because the infusion device 1 has a comparatively small size and in particular a flat shape, it may be placed, together with other infusion devices 1, in a space-efficient manner at the bedside of a patient, as it is illustrated in FIG. 7. A holding device 3 in this case may be constituted to hold multiple infusion devices 1 in parallel such that each infusion device 1 is attached in-between connection fingers 310, 320 of a respective pair of arms 31, 32 and, hence, may be individually pivotable with respect to the holding device 3.

Figure 8C:
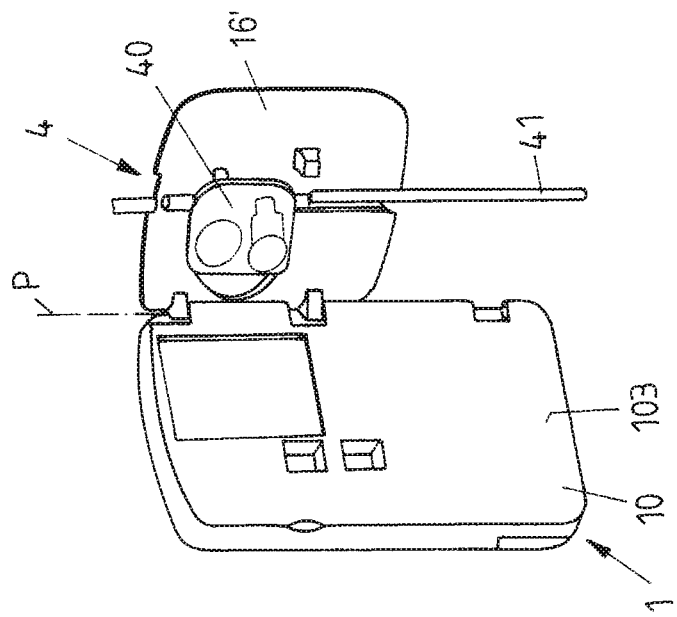
FIG. 8C shows a back view of the infusion device, with a back part of the infusion device being opened.
Figure 8B:
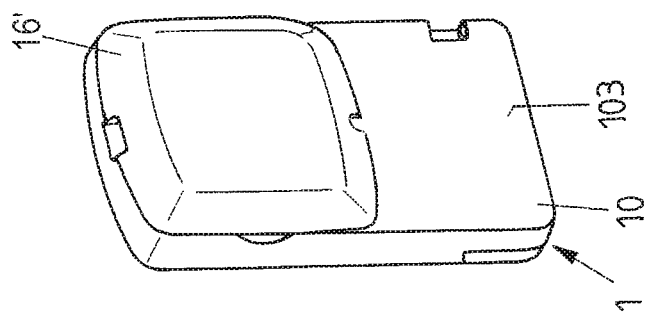
FIG. 8B shows a back view of the infusion device.
Figure 8A:
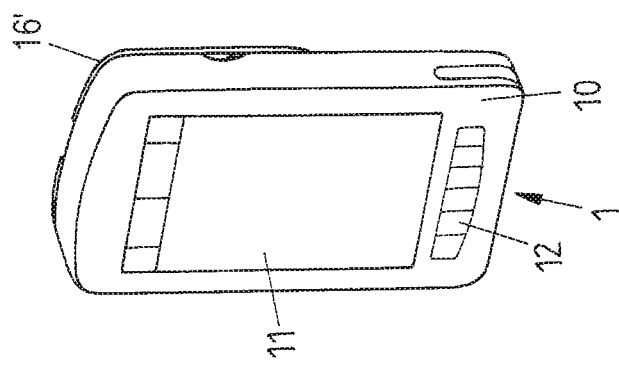
FIG. 8A shows a front view of another embodiment of an infusion device.

Another embodiment of an infusion device 1 is shown in FIG. 8A-8C and 9A-9C. Again, the infusion device 1 may be used together with a back part 16' of a first type, as shown in FIG. 8A-8C, or together with a back part 17' of a second type, as shown in 9A-9C. The back part 16' serves to attach a disposable pump module 4 in the shape of an infusion set to the infusion device 1. The back part 17', in contrast, comprises a fluid container to which an infusion line may be connected via an attachment opening 171 in order to pump the medical fluid contained in the back part 17' towards a patient. A membrane 170 having a ring shape is located at the inside of the back part 17' and, in a closed position of the back part 17' (FIG. 9B), is in interaction with a pump mechanism arranged inside the housing 10 such that a pumping of the medical fluid out of the back part 17' can be effected.

The infusion device 1 as shown in FIG. 8A-8C and 9A-9C, although differing in its outwards design, is functionally identical to the embodiment described before such that it shall be referred to the above.

Figure 10:
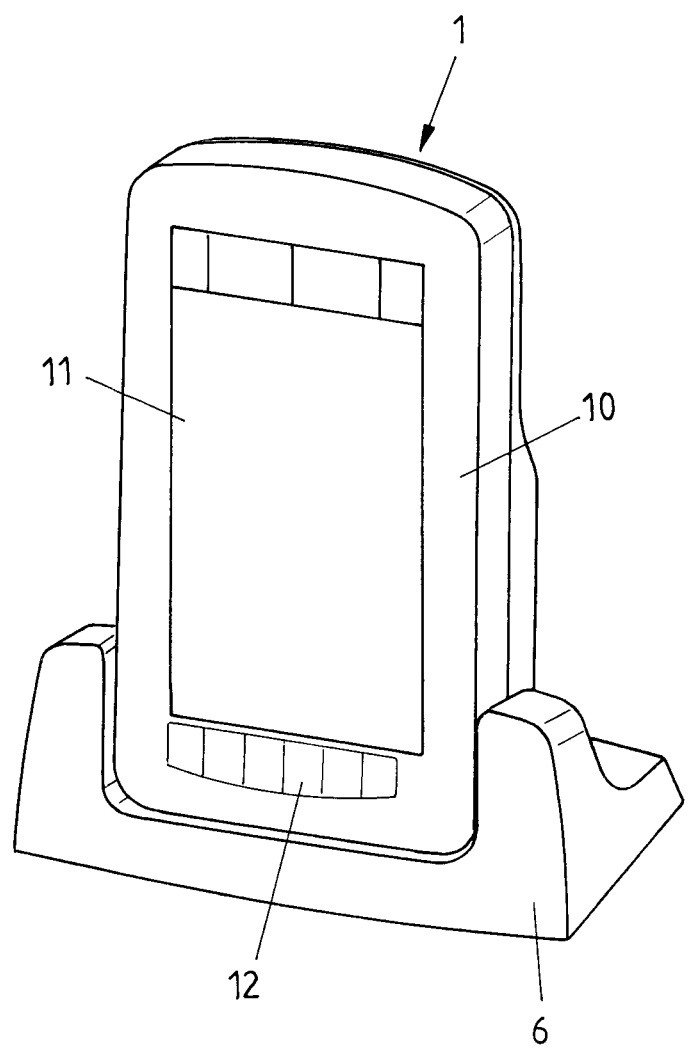
FIG. 10 shows a view of an infusion device on a docking station.

The infusion device 1 of the embodiment according to FIG. 1 to 7 or according to the embodiment of FIG. 8A-8C and 9A-9C may be constituted to operate in an autarkic fashion in that, when performing an actual infusion operation on a patient, no connection to an external power supply line is necessary, but electrical energy is supplied to the pump mechanism 18 from the battery device 182 contained in the housing 10. In order to recharge the battery device 182, the infusion device 1 may be placed, as shown in FIG. 10, on a docking station 6, the docking station 6 for example comprising appropriate connectors to contact corresponding connectors of the infusion device 1 to supply electrical energy to the battery device 182. In addition, a data connection may be provided via the docking station 6 such that data can be read out from the infusion device 1 and may be transferred for example to external devices, for example via an external communication network such as a hospital information network.

The idea underlying the invention is not limited to the embodiments described above.

In particular, infusion devices may also have a different shape and may be used in connection with different back parts.

Infusion devices of the kind described above may be employed for different purposes and in different environments, in particular in healthcare environments, to deliver medical fluids, for example a medication fluid, a saline solution, a nutritional liquid or any other fluid, to a patient.

LIST OF REFERENCE NUMERALS

1 Infusion device
10 Housing
100 Top side
101 Bottom side
102 Front side
103 Back side
104, 105 Mounting recess
11 Display device
12 Input device
13 Key
14 Loudspeaker
15 Button
16 Back part
160, 161 Opening
162 Reception channel
163 Reception opening
17 Disposable part (drug container)
170 Pump section (membrane)
171 Attachment opening
18 Pump mechanism
180 Wobble device
181 Drive device
182 Battery device
183 Actuation mechanism
184 Connectors
2 Stand
3 Holding device
30 Base
31, 32 Arm
310, 320 Connection finger
33 Clamping device
330 Connection piece
34 Clamping screw
4 Disposable pump module
40 Pump cassette
400 Pump section (membrane)
41 Infusion line
5 Infusion container
6 Docking station
A Adjustment direction
P Pivot axis
S Pivot axis
T Pivot axis

The invention claimed is:

1. An infusion device, comprising:
a housing having a front side and a back side opposite to the front side, the housing having a generally flat shape with a thickness measured along a thickness direction in between the front side and the back side being smaller than a height measured between a top and a bottom of the housing and a width measured in between lateral sides of the housing;
a display device arranged at the front side of the housing;
a pump mechanism for acting onto a disposable pump module, the pump mechanism being included in the housing; and
a back part connectable to the housing, wherein the back part in a connected state is pivotable with respect to the housing and wherein the back part is configured to be selectably releasable from the housing to replace the back part by at least one additional back part that includes the disposable pump module and a fluid container containing a medical fluid for administration to a patient,
wherein the back part and the at least one additional back part, are selected from at least two of the configurations of:
(a) a first back part and the fluid container is a separate pump cassette, and the first back part when releasably attached holds the pump cassette internally between the first back part and the housing, the first back part and the back side of the housing comprise a reception channel forming a first opening for allowing an infusion line connected to said pump module to enter said reception channel, and a second opening allowing said infusion line to exit from the reception channel,
(b) a second back part and the fluid container is a first medication bag attached to the second back part with a first medical fluid line in fluid communication with the first medication bag, the second back part and the back side of the housing comprise a reception channel forming a first opening for allowing an infusion line connected to said pump module to enter said reception channel, and a second opening allowing said infusion line to exit from the reception channel, (c) a third back part wherein the third back part comprises the fluid container formed on the third back part, and the third back part comprises an attachment opening for attaching an infusion line in fluid communication with the third back part, and (d) a fourth back part and the fluid container is a separate pump cassette, and the fourth back part when releasably attached holds the pump cassette internally between the fourth back part and the housing, the fourth back part and the back side of the housing comprise a reception channel forming a first opening for allowing an infusion line connected to said pump module to enter said reception channel, and a second opening allowing said infusion line to exit from the reception channel and an end of the infusion line is attached to a medication bag in fluid communication with the separate pump cassette;

wherein the housing is configured to receive the disposable pump module at the back side, and wherein the back part in a closed position covers at least a portion of the back side, the back part and the back side of the housing together forming a receptacle for receiving the disposable pump module, wherein the back part together with the housing is configured to receive the disposable pump module in the receptacle such that the disposable pump module in the closed position of the back part is held on the infusion device.

2. The infusion device according to claim 1, wherein the pump mechanism comprises a wobble device for performing a wobbling movement for acting onto the disposable pump module.

3. The infusion device according to claim 1, wherein the infusion device comprises a battery device for storing electrical energy.

4. A system comprising an infusion device according to claim 1 and a holding device for holding the infusion device, the holding device being configured to hold the infusion device such that the infusion device is pivotable with respect to the holding device about a first pivot axis.

5. The system according to claim 4, wherein the holding device comprises a base and at least one arm extending from the base in a direction parallel to the first pivot axis, the at least one arm comprising a connection finger at an end opposite to the base for pivotably connecting the infusion device to the holding device.

6. The system according to claim 5, wherein the connection finger is configured to reach around a top side or a bottom side of the housing of the infusion device, the top side and the bottom side being arranged, when viewed along the first pivot axis, opposite to each other on the housing.

7. The system according to claim 5, wherein the holding device comprises a clamping device for connecting the holding device to a stand, the base being pivotably connected to the clamping device such that the base is pivotable with respect to the clamping device about a second pivot axis oriented transversely to the first pivot axis.

8. A system for forming an infusion device, comprising:

a housing having a front side and a back side opposite to the front side, the housing having a generally flat shape with a thickness measured along a thickness direction in between the front side and the back side being smaller than a height measured between a top and a bottom of the housing and a width measured in between lateral sides of the housing;

a display device arranged at the front side of the housing;

a pump mechanism for acting onto a disposable pump module, the pump mechanism being included in the housing; and a plurality of back parts, wherein each of the plurality of back parts is individually connectable to the housing for forming the infusion device, and wherein each of the plurality of back parts is releasable from the housing to replace the connected back part by at least one additional back part of the plurality of back parts; and wherein each of the plurality of back parts in a connected state is pivotable with respect to the housing;

wherein the housing is configured to receive the disposable pump module at the back side;

wherein each of the plurality of back parts in a closed position covers at least a portion of the back side;

wherein at least one of the plurality of back parts is configured such that the at least one back part and the back side of the housing together form a receptacle for receiving the disposable pump module, wherein the at least one back part together with the housing is configured to receive the disposable pump module in the receptacle such that the disposable pump module in the closed position of the at least one back part is held on the infusion device, wherein the plurality of back parts comprises the disposable pump module and a fluid container containing a medical fluid for administration to a patient, wherein the plurality of back parts, including the at least one additional back part, are selected from at least two of the configurations of:

(a) a first back part and the fluid container is a separate pump cassette, and the first back part when releasably attached holds the pump cassette internally between the first back part and the housing, the first back part and the back side of the housing comprise a reception channel forming a first opening for allowing an infusion line connected to said pump module to enter said reception channel, and a second opening allowing said infusion line to exit from the reception channel, (b) a second back part and the fluid container is a first medication bag attached to the second back part with a first medical fluid line in fluid communication with the first medication bag, the second back part and the back side of the housing comprise a reception channel forming a first opening for allowing an infusion line connected to said pump module to enter said reception channel, and a second opening allowing said infusion line to exit from the reception channel, (c) a third back part wherein the third back part comprises the fluid container formed on the third back part, and the third back part comprises an attachment opening for attaching an infusion line in fluid communication with the third back part, and (d) a fourth back part and the fluid container is a separate pump cassette, and the fourth back part when releasably attached holds the pump cassette internally between the fourth back part and the housing, the fourth back part and the back side of the housing comprise a reception channel forming a first opening for allowing an infusion line connected to said pump module to enter said reception channel, and a second opening allowing said infusion line to exit from the reception channel and an end of the infusion line is attached to a medication bag in fluid communication with the separate pump cassette.

9. The system according to claim 8, wherein the fluid container contains at least one of a medication fluid, a saline solution, and a nutritional liquid.

\* \* \* \* \*